(12) United States Patent
Harfert

(10) Patent No.: US 8,870,022 B2
(45) Date of Patent: Oct. 28, 2014

(54) DIAPER AND WIPE DISPENSING SYSTEM

(76) Inventor: Stacy Harfert, Arvada, CO (US)

( * ) Notice: Subject to any disclaimer, the term of this patent is extended or adjusted under 35 U.S.C. 154(b) by 50 days.

(21) Appl. No.: 13/103,777

(22) Filed: May 9, 2011

(65) Prior Publication Data

US 2011/0272429 A1 Nov. 10, 2011

Related U.S. Application Data

(60) Provisional application No. 61/332,453, filed on May 7, 2010.

(51) Int. Cl.
*B65D 83/00* (2006.01)
*A61F 15/00* (2006.01)

(52) U.S. Cl.
CPC ..................................... *A61F 15/001* (2013.01)
USPC ................................ 221/130; 221/45; 221/92

(58) Field of Classification Search
USPC ......... 221/34, 45, 46, 56, 61, 62, 69, 92, 123, 221/124, 130, 281–283
See application file for complete search history.

(56) References Cited

U.S. PATENT DOCUMENTS

| | | | | |
|---|---|---|---|---|
| 1,904,777 A * | 4/1933 | Brzezicki | ...................... | 206/237 |
| 1,989,381 A * | 1/1935 | Samson | ........................... | 221/56 |
| 2,421,342 A * | 5/1947 | MacKenzie | ...................... | 221/34 |
| 2,738,898 A * | 3/1956 | Lee | ................................. | 221/35 |
| D316,788 S * | 5/1991 | Fischer et al. | ................. | D6/522 |
| 5,752,622 A * | 5/1998 | Abell | ............................. | 221/97 |
| 5,873,542 A * | 2/1999 | Perrin et al. | .................. | 242/560 |
| 6,427,839 B1 * | 8/2002 | Helfer-Grand | ................ | 206/494 |
| 6,557,723 B2 * | 5/2003 | Chen | ................................. | 221/45 |
| 7,044,329 B2 * | 5/2006 | Lum et al. | ....................... | 221/45 |
| 7,222,747 B1 * | 5/2007 | Savran | ............................ | 221/34 |
| 7,789,236 B2 * | 9/2010 | Burgess | ........................ | 206/494 |
| 8,561,837 B2 * | 10/2013 | Giammanco | ................. | 221/102 |
| 2005/0033259 A1 * | 2/2005 | Stravitz | ........................ | 604/403 |
| 2006/0027591 A9 * | 2/2006 | Sanders et al. | .................. | 221/59 |
| 2006/0091146 A1 * | 5/2006 | Boulet-Mazer | ................. | 221/34 |
| 2007/0045333 A1 * | 3/2007 | Mitchell et al. | ................. | 221/34 |
| 2007/0284387 A1 * | 12/2007 | Ellswood et al. | .............. | 221/92 |
| 2008/0223867 A1 * | 9/2008 | Carr | ................................ | 221/34 |
| 2009/0152161 A1 * | 6/2009 | St. Cyr | .......................... | 206/581 |
| 2009/0223992 A1 * | 9/2009 | Lorenzati et al. | .............. | 221/34 |
| 2011/0266299 A1 * | 11/2011 | Fodor | ............................ | 221/102 |
| 2011/0297694 A1 * | 12/2011 | Conway et al. | ................. | 221/46 |
| 2011/0315707 A1 * | 12/2011 | Kleinhuber | .................... | 221/155 |
| 2012/0032565 A1 * | 2/2012 | Stoop et al. | .................. | 312/34.4 |
| 2012/0074193 A1 * | 3/2012 | Efthimiadis | .................... | 225/39 |
| 2012/0228322 A1 * | 9/2012 | Comerford | ..................... | 221/34 |
| 2014/0103058 A1 * | 4/2014 | Schiering et al. | ............... | 221/34 |

OTHER PUBLICATIONS

JJ Cole Collections, Diaper Stacker, http://jjcolecollections.com/diaper-stacker, 2011.

\* cited by examiner

*Primary Examiner* — Gene Crawford
*Assistant Examiner* — Kelvin L Randall, Jr.

(57) ABSTRACT

A diaper and wipe dispensing system includes a housing with an upper compartment for accommodating stacked diapers and a lower compartment separated from the upper compartment, for accommodating baby wipes. A diaper slot in the housing facilitates access to diapers within the upper compartment, and a wipe slot in the housing allows access to wipes within the lower compartment. At least one access panel releasably secures with the housing, such that diapers and wipes are loaded into the housing via the at least one access panel. The housing may be formed by a wall plate and a cover that slidably mates with the cover via lock-and-key features.

20 Claims, 15 Drawing Sheets

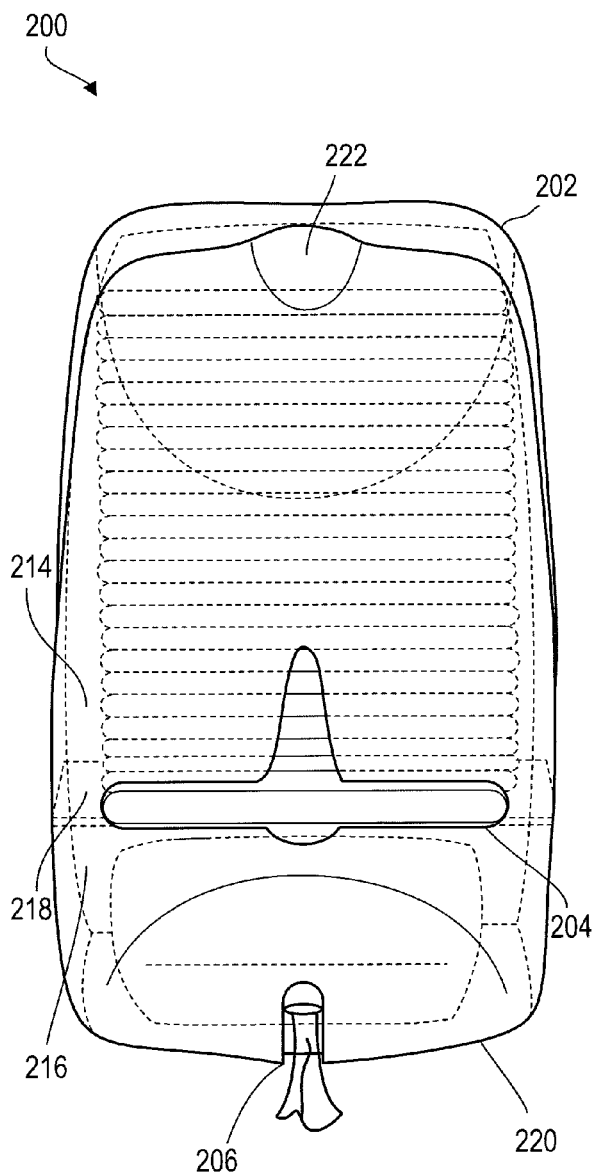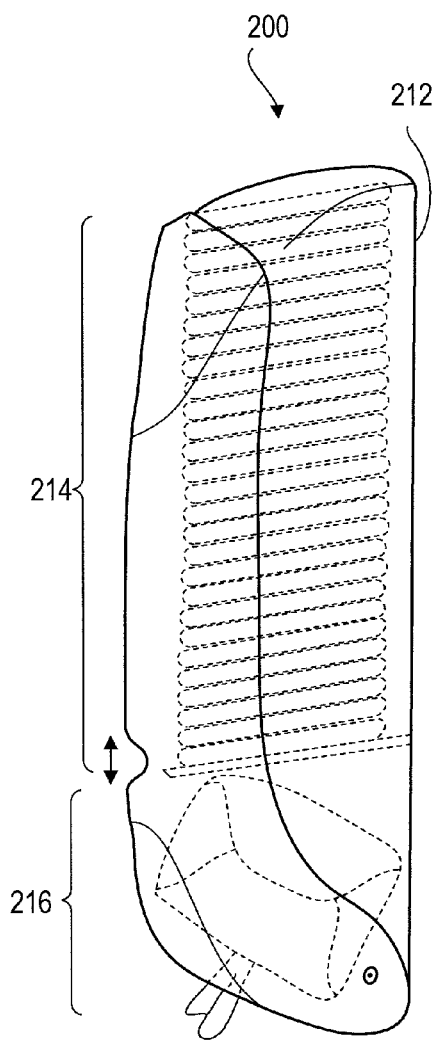
FIG. 5
FIG. 6

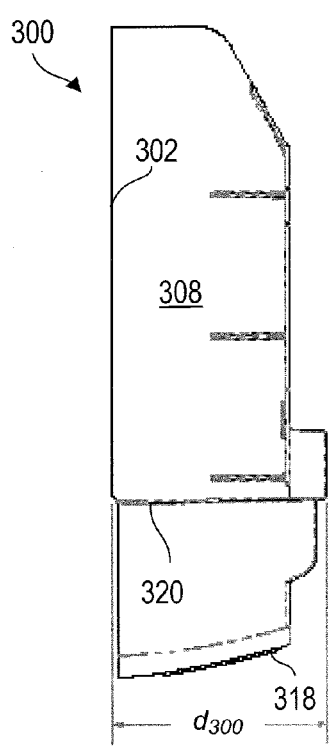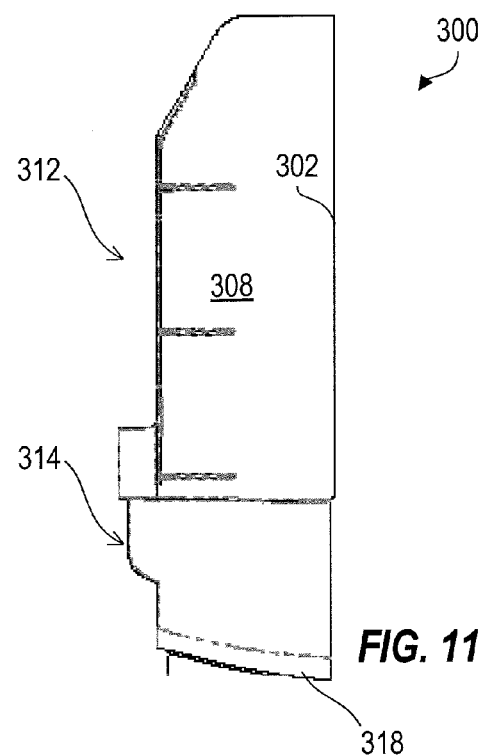

DIAPER AND WIPE DISPENSING SYSTEM

RELATED APPLICATIONS

This application claims priority to U.S. Provisional Patent Application No. 61/332,453, filed May 7, 2010, which is incorporated herein by reference.

BACKGROUND

Milton Berle once quipped, "If evolution really works, how come mothers only have two hands?" Mothers, and others who care for babies, often juggle a baby in one hand while handling a myriad of tasks with the other. For example, when changing a baby's diaper, the caregiver should always keep one hand on the baby to prevent falls from the changing table. The other hand is responsible for removing the soiled diaper, popping open the wipe dispenser, wrestling wipes (which do not always self-feed) from the dispenser, cleaning the baby's bottom, getting and arranging a new diaper under the baby and securing the new diaper to the baby.

In efforts to make the diapering process easier, fabric diaper stackers can be purchased or made, and hung on a wall near the changing table or on the changing table itself. However, these stackers tend to move with the diapers. In other words, when a user tries to pull a diaper from the stacker, the stacker follows—either clinging about the user's hand, clinging about the diaper or lifting off of the wall or changing table, sometimes resulting in diapers falling from the stacker and onto the floor. Even when stackers remain in place, the user still must separately obtain baby wipes in order to clean the baby.

SUMMARY

The diaper and wipe dispensing system disclosed herein provides a solution to conventional and cumbersome diapering aids.

In one embodiment, a diaper and wipe dispensing system includes a housing with an upper compartment for accommodating stacked diapers and a diaper slot in the housing, for accessing diapers within the upper compartment. A lower compartment within the housing and separated from the upper compartment, accommodates baby wipes. A wipe slot in the housing, allows access to wipes within the lower compartment. At least one access panel releasably secures with the housing, wherein diapers and wipes are loaded into the housing via the at least one access panel.

In one embodiment, a diaper and wipe dispensing system includes a housing formed by a rear wall plate for mounting with a vertical surface, and a front cover configured to slidably mate with the rear wall plate. An upper compartment within the housing holds stacked diapers, and a diaper slot in the housing allows access to diapers within the upper compartment. A lower compartment within the housing and separated from the upper compartment by a floor panel holds baby wipes; and a wipe slot in the housing allows access to wipes within the lower compartment. The cover slides down with respect to the wall plate to secure the cover with the wall plate and slides up with respect to the wall plate to facilitate removal of the cover and loading of diapers and wipes.

BRIEF DESCRIPTION OF THE DRAWINGS

FIG. 5 is a front plan view showing exemplary dimensions of a diaper and wipe dispensing system, according to an embodiment.

FIG. 6 is a side view of the system of FIG. 5.

FIGS. 10 and 11 are side views of the wall plate of FIGS. 7-9.

DETAILED DESCRIPTION

Figure 1:
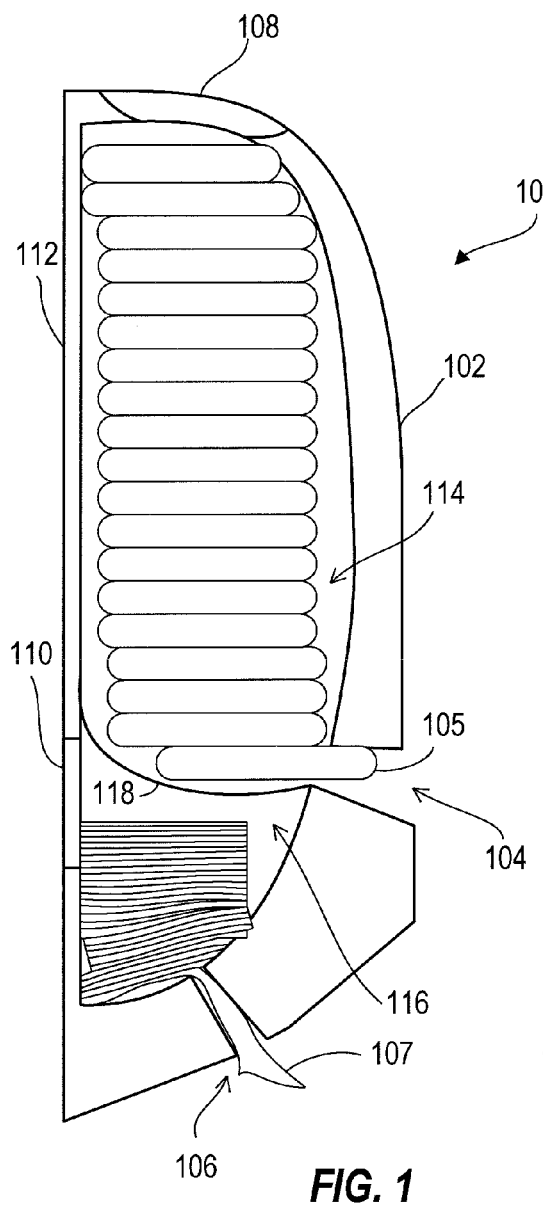
FIG. 1 is a simplified, cross-sectional view through a side of a diaper and wipe dispensing system, according to an embodiment.
Figure 2:
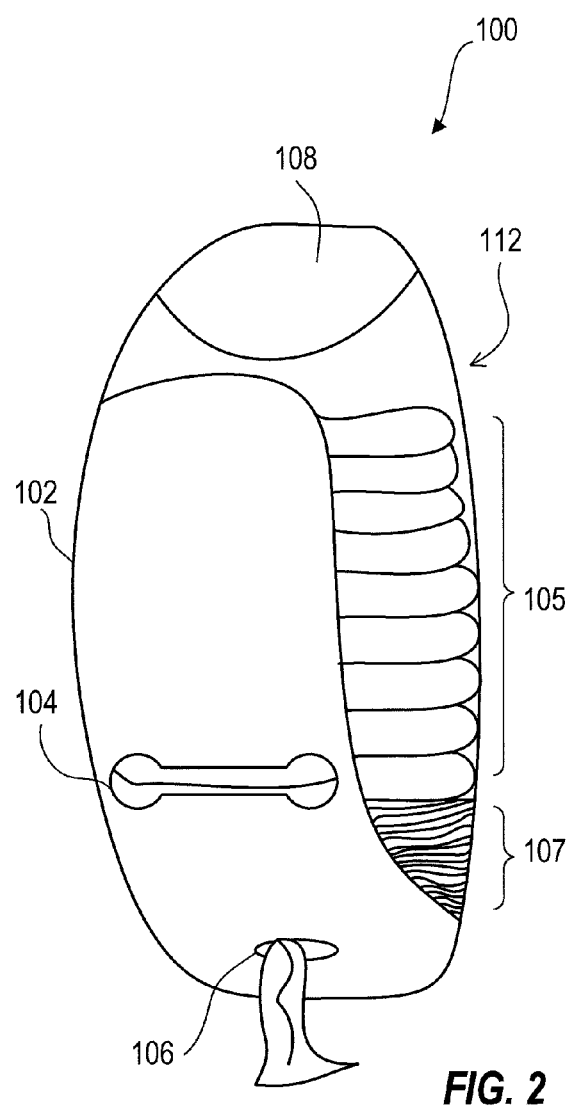
FIG. 2 is a side perspective view of the system of FIG. 1.
Figure 3:
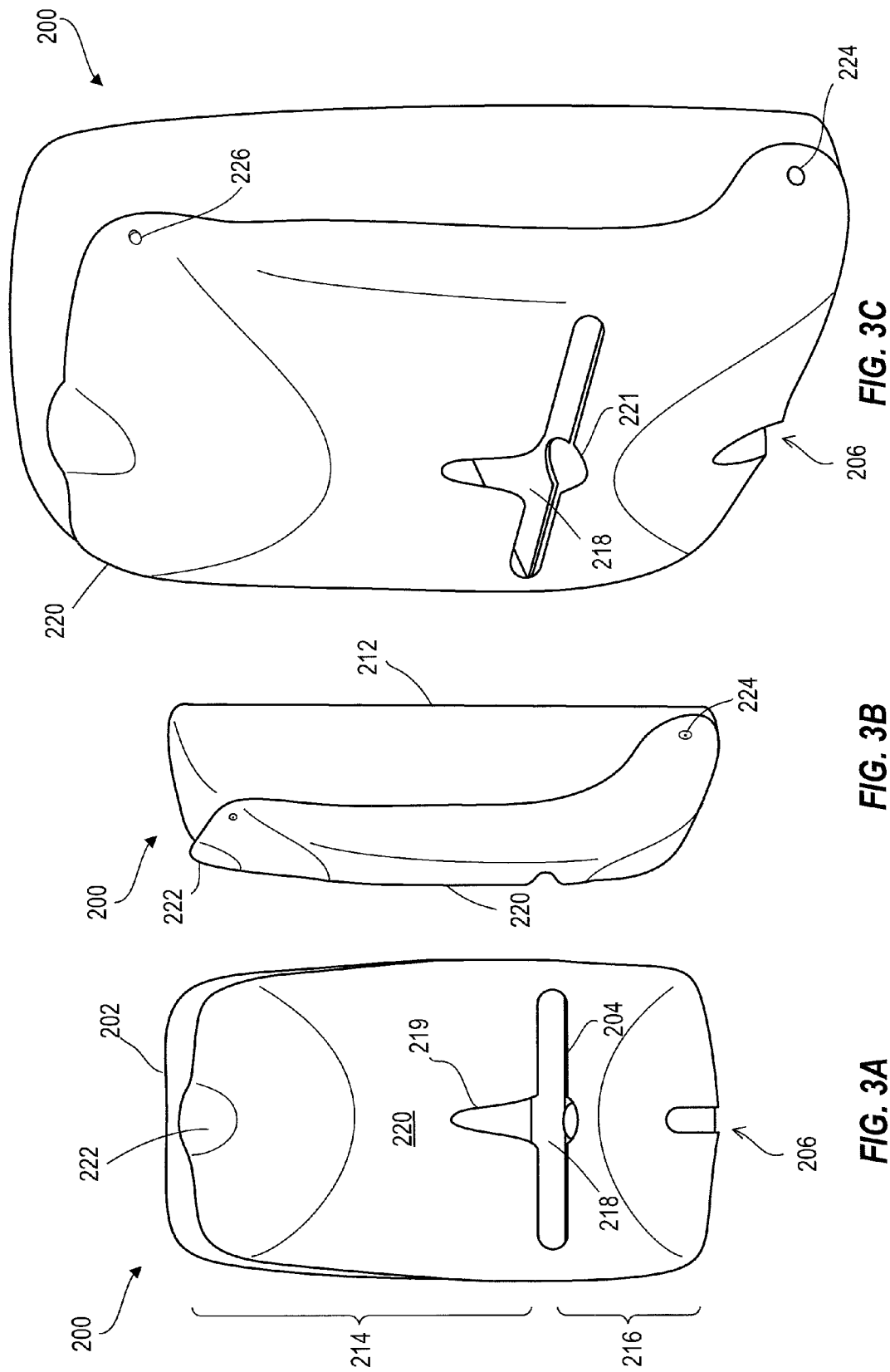
FIGS. 3A-3C are schematic front, side and perspective views of a diaper and wipe dispensing system, according to an embodiment.
Figure 4:
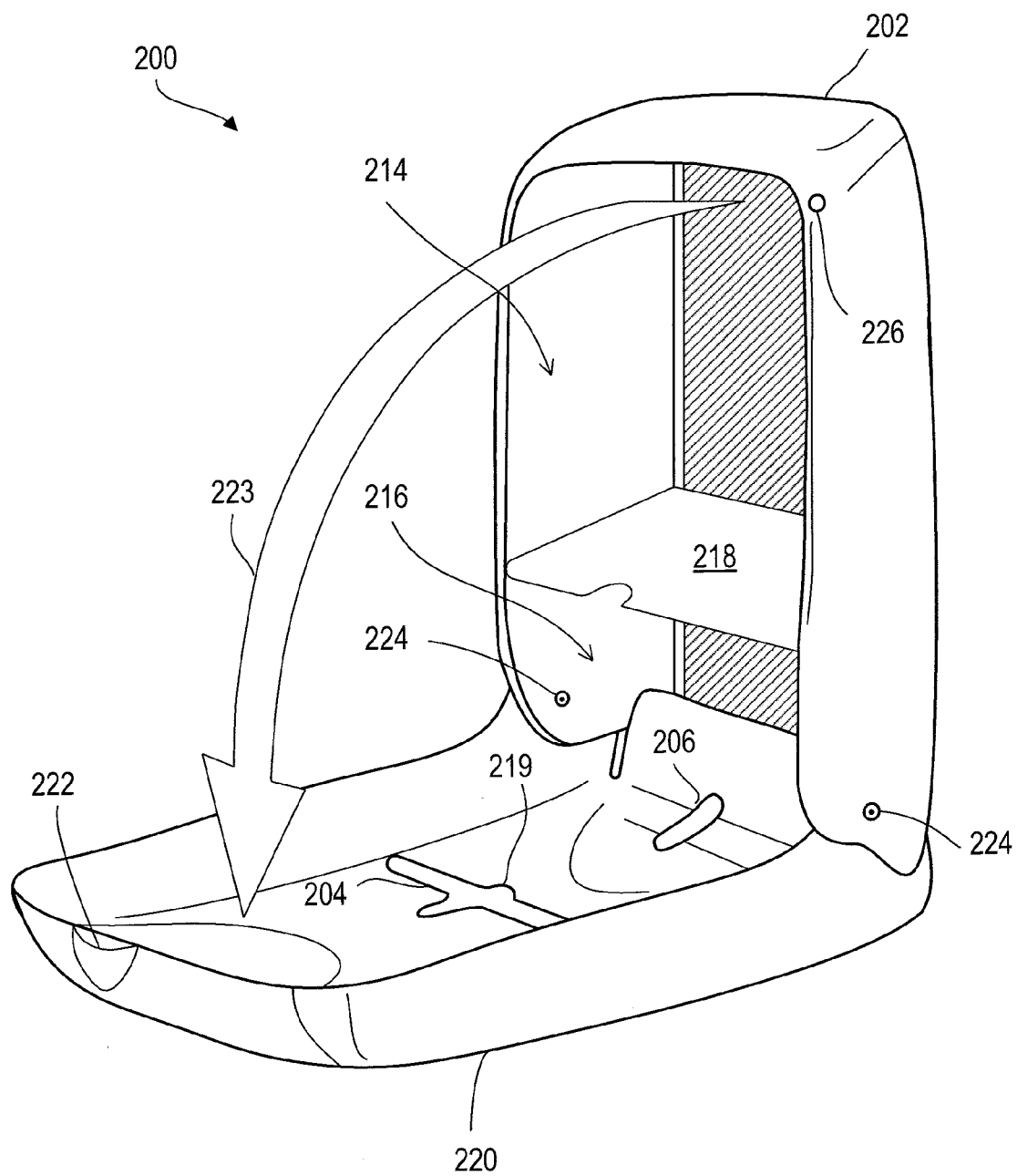
FIG. 4 is a perspective view showing the system of FIGS. 3A-3C in an open position.

FIGS. 1 and 2 show a diaper and wipe dispensing system 100. System 100 having a housing 102 with diaper and wipe retrieval slots 104 and 106, for accessing diapers 105 and wipes 107, respectively. Diapers 105 are loaded into housing 102 via a door or opening 108 that is for example on the top of housing 102. In one aspect, baby wipes are inverted and loaded into housing 102 via door or opening 110, which may be on a back 112 or side (not shown) of housing 102. Baby wipes may be removed from the hard container or flexible sleeve in which they are purchased, or may be retained in the sleeve or container, as the compartment holding the wipes is shaped to align the sleeve opening with slot 106. Doors 108 and 110 may be hinged doors, sliding doors, spring-assisted doors that open when pressed, or any other known access door that is compatible with housing 102. Optionally, as shown and described with respect to later figures, the entire front or a side of housing 102 may form one or more access panels for loading diapers 105 and wipes 107.

Diapers 105 are held within an upper compartment 114, separated from a lower wipe compartment 116 by a floor panel 118. Panel 118 forms a shelf upon which diapers may be stacked horizontally. In one aspect, wipe compartment 116 is a backless compartment, open to a wall-mounting side of system 100, and wipes may be loaded into wipe compartment 116 via the above-described doors or from the open back. Contact or proximity between the back of system 100 and a wall or surface with which system 100 mounts maintains sufficient closure of wipe compartment 116 to maintain moisture within compartment 116, thus keeping stored baby wipes moist.

When one diaper 105 is removed from housing 102 via slot 104, any diapers stacked thereon drop down, making a second and subsequent diapers available for retrieval through slot 104. Likewise, when lower compartment 116 is supplied with a stack of inverted, self-feeding wipes 107, pulling one wipe 107 through slot 106 automatically advances a second wipe to a position where it may also be retrieved through slot 106. Advantageously, because wipes 107 are inverted and retrieved from below or laterally (as opposed to conventional wipe cartons, where wipes are pulled from above), gravity aids in advancing subsequent wipes to retrieval position, limiting separation of wipes from one another and enhancing any self-feeding orientation.

In one aspect, housing 102 is made with a rigid material such as ABS plastic (e.g., one free of BpA, phthalates and PVC), although metal, wood, chip board, and other rigid materials may also form housing 102. Material forming housing 102 may also be covered with decorative fabric, decals or another ornamental covering. Because housing 102 is rigid, back 112 remains affixed to whatever surface it is attached, eliminating excess movement in system 100.

FIGS. 3A-3C and FIGS. 4-6 show a diaper and wipe dispensing system 200. For clarity of illustration, not all components of system 200 are shown in each Figure, thus, the Figures are best viewed together with the following description.

System 200 includes a housing 202, a diaper retrieval slot 204 opening into an upper, diaper storage compartment 214, and a wipe retrieval slot 206 opening into a lower, wipe storage compartment 216. System 200 may be made from plastic, for easy cleaning; however, other materials may be used (for example, metal), without departing from the scope hereof. In one embodiment, system 200 is approximately 18-19" tall, 10-11" wide and 6" deep; diaper slot 204 is about 1" tall by 9" wide, and wipe slot 206 is an oval shaped slot having a width of about 1". It will be appreciated that these dimensions may vary as a matter of design preference. System 200 is compatible with either disposable or cloth diapers of any size.

Wipe retrieval slot 206 is oriented on a lower, front panel of housing 202 and is for example shaped as a thin oval to minimize exposure of wipes to outside air. Such orientation and shape may likewise prevent fluid saturating the wipes from leaking out of system 200 and onto the floor below. In one aspect, wipes stack directly upon a floor of wipe storage compartment 216, beneath retrieval slot 206. In another aspect, system 200 may include a small lower reservoir (not shown) beneath or included with wipe storage compartment 216, for capturing any fluid that drains from the wipes and any sleeve or rigid container in which they are held (see, e.g., FIG.

6). In one aspect, compartment 216 has a screen, mesh, or slotted false floor above the reservoir, for supporting the wipes and allowing fluid drainage. Alternately or additionally, slot 206 is covered by a cover (not shown) that may be hingedly attached with a front panel 220, or which snaps into slot 206 or otherwise fits over slot 206, to maintain moisture content of the wipes when slot 206 is closed. Compartment 216 is shaped to align any slot of a wipe sleeve or hard wipe container with slot 206, or, as noted, wipes may be removed from such sleeve or container and loaded directly into compartment 216.

Compartments 214 and 216 are separated by a floor panel 218 (see FIG. 3C) forming a shelf for horizontally stacked diapers. Diapers may be stacked in one or more horizontal "columns", according to the dimensions of housing 200 and retrieval slot 204. As shown, retrieval slot 204 may include a vertically-oriented cutout 219 to accommodate a user's forefinger and thumb as the user grasps a stacked diaper through slot 204. Floor panel 218 may likewise include a cutout 221 to further aid a user grasping the diaper with the thumb and forefinger.

Front panel 220 may include a finger or thumb catch 222 to facilitate opening. In one aspect, panel 220 opens as indicated by arrow 223, by pivoting or hinging about lower pivot points 224. However, it will be appreciated that panel 220 may alternately hinge at a side, or even the top, of housing 200.

Locking buttons, switches, snaps or other releasable locking mechanisms 226 may be included at the sides of panel 220 and/or elsewhere on housing 202, to secure panel 220 in place when closed. In one aspect, panel 220 and housing 202 are shaped with complimentary lock and key features at their borders, such that panel 220 snaps shut with housing 202. Diapers and baby wipes (e.g., diapers 105 and wipes 107) are loaded into respective compartments 214 and 216 when front panel 220 is opened, and accessible via respective slots 204 and 206 in front panel 220 when front panel 220 is closed.

A back side 212 of system 200 may be mounted to a wall, changing table, dresser or other (preferably vertical or near-vertical) surface using conventional fasteners (e.g., one or more locking channels designed to accommodate and secure system 200 to a screw). System 200 may advantageously be hung on a wall, out of reach of children yet still in reach of an adult changing the baby's diaper. System 200 allows the user to keep one hand on the baby while freeing the other hand to retrieve wipes and diapers as needed, eliminating the need to (a) pop open a wipe container and deal with wipe separation and shredding endemic to such containers, and (b) wrestle with a separate cloth diaper stacker, drawer or basket to retrieve a diaper.

It will be appreciated that FIGS. 1-6 show illustrative examples of systems 100 and 200. Systems 100 and 200 and their components are not limited to the particular shapes and dimensions shown in the figures or described herein above. It will be appreciated that many changes and modifications may be made to the disclosed diaper and wipe dispensing systems, without departing from the spirit and scope of this invention. For example, wipe slots 106 and/or 206 may include a cover that is opened or removed to access stacked wipes within respective system 100/200, to maintain moisture content of the baby wipes when system 100/200 is not in use.

Figure 7:
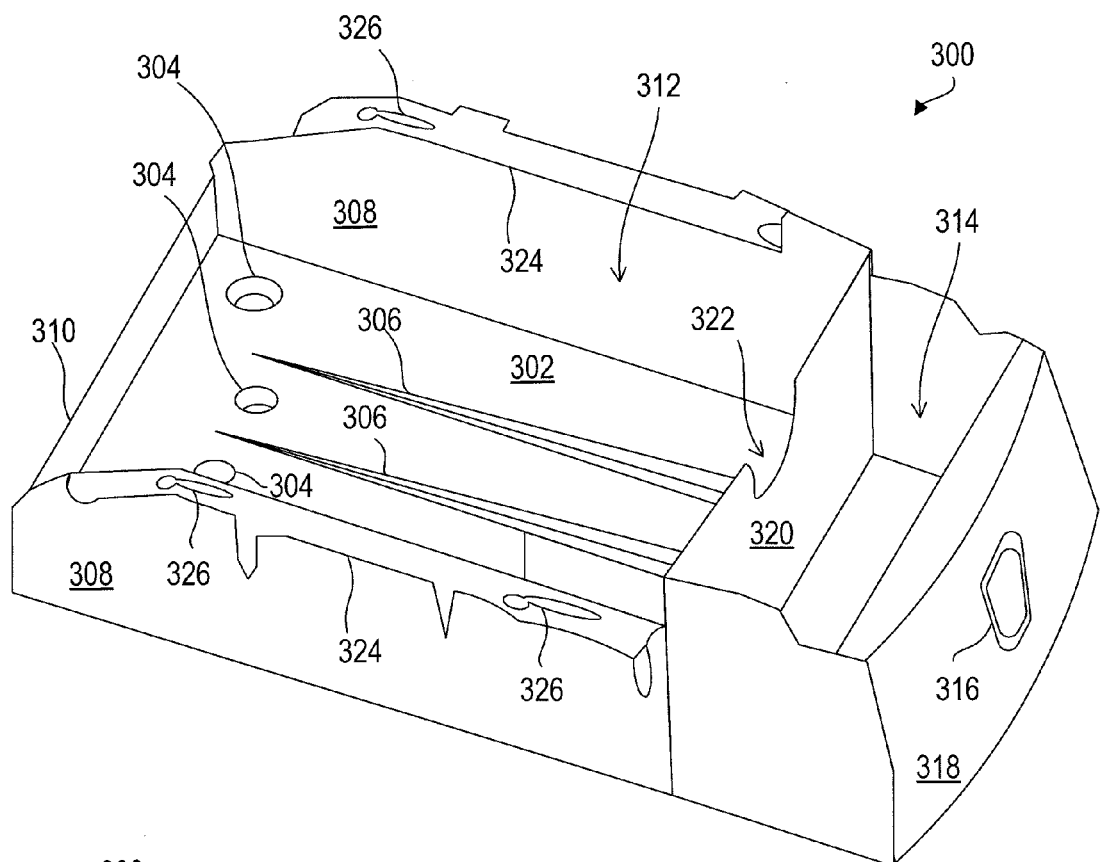
FIG. 7 is a front perspective view of a wall plate forming a back side and partial sides, top and base of a diaper and wipe dispensing system.
Figure 8:
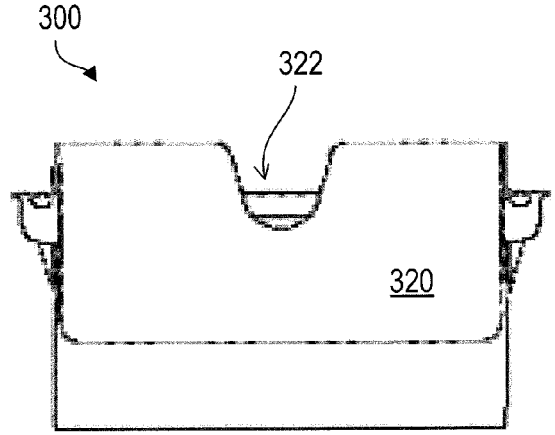
FIG. 8 is a simplified end view of a diaper compartment of the wall plate of FIG. 7.
Figure 9:
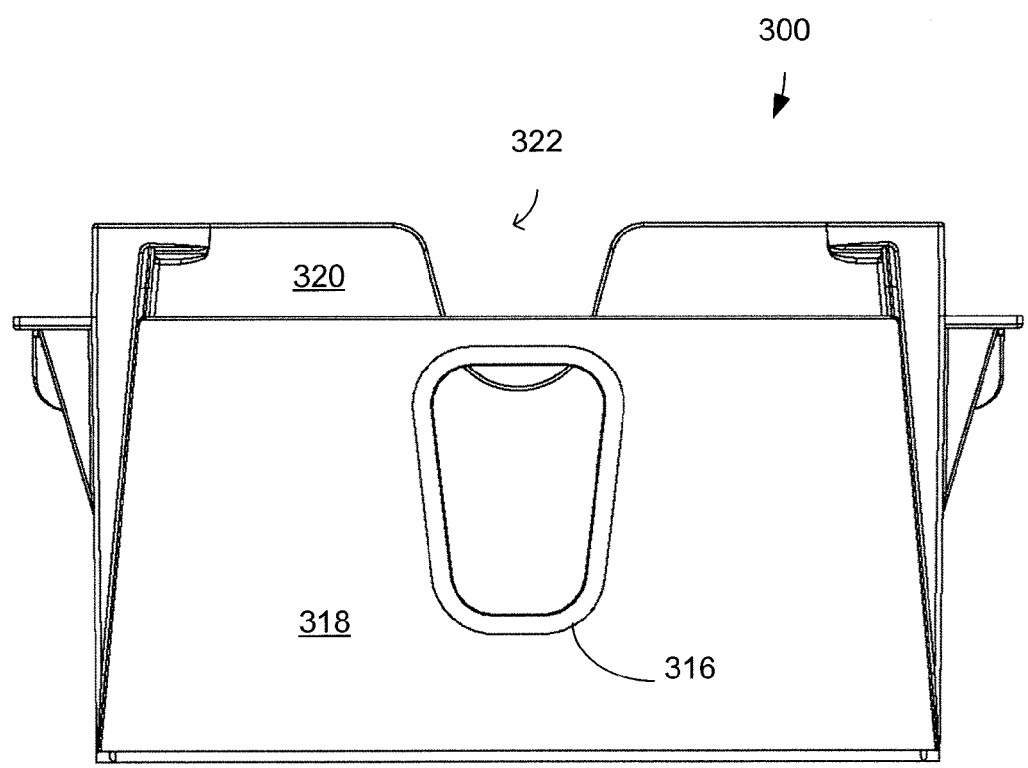
FIG. 9 is a simplified end view showing the diaper compartment of FIG. 8 configured with a wipes compartment of the wall plate of FIG. 7.

In one aspect, a diaper and wipe dispensing system includes a wall plate 300, as illustrated in FIGS. 7-13. As shown in FIG. 7, wall plate 300 includes a back panel 302 having one or more wall mounting features 304 for variable mounting with a vertical wall. Features 304 are for example apertures for mounting wall plate 300 with a wall using drywall screws and drywall anchors, or for screwing or nailing plate 300 to a wall stud. Raised ribs 306, shown within wall plate 300, extend progressively outward, top to bottom, from back panel 302, to push shuttle stacked diapers forward towards a diaper retrieval slot in a cover that mates with wall plate 300 (see, e.g., description of cover 400 and diaper retrieval slot 404, below).

Wall plate 300 includes sidewalls 308 and a ceiling 310 which, together with back panel 302 (and a floor panel described below) form a diaper compartment 312 for supporting stacked diapers and a lower wipe compartment 314 for holding stacked baby wipes. Wipe compartment 314 forms a wipe retrieval slot or aperture 316 for accessing wipes stored within compartment 314. In one aspect, wipe retrieval slot 316 is formed along a downward curving or tapering (when mounted with a vertical wall) base 318 of wall plate 300, about 1-1.5 inches from back panel 302. Compartments 312 and 314 are separated by a horizontal (when mounted) floor panel 320 of diaper compartment 312, which may include a cutout 322 to aid a user grasping a diaper within compartment 312 with the thumb and forefinger. See also FIGS. 8 and 9 for end views of wall plate 300 showing downward curving base 318, wipe retrieval slot 316, floor panel 320 and cutout 322. Back panel 302 may terminate at floor panel 320, leaving wipe compartment 314 open at the back, such that a wall or surface with which wall plate 300 mounts "closes" compartment 314 at the back and facilitates moisture retention within compartment 314. Optionally, back panel 302 extends to curving base 318 to close the back side of compartment 314.

Wall plate 300 may include a pair of lateral shelves 324 with each shelf 324 having one or more cutouts or apertures 326 complementary to mating features in a dispenser cover (such as cover 400, described below). In one aspect, a dispenser cover slides downward onto shelves 324 to mount with wall plate 300, for example, once wall plate 300 is secured with a vertical wall or other vertical surface.

Figure 12:
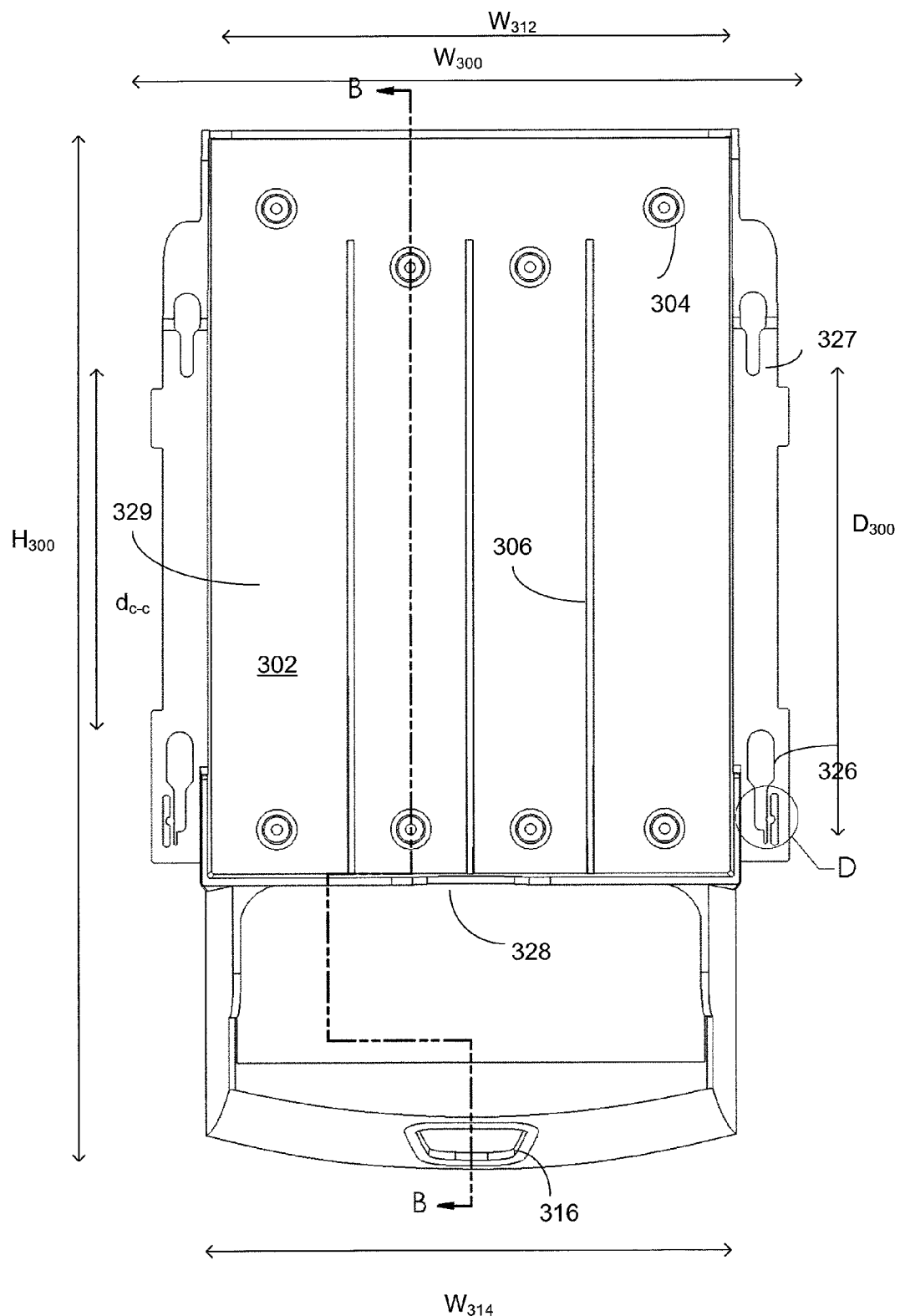
FIG. 12 is a rear view of the wall plate of FIGS. 7-11.
Figure 13:
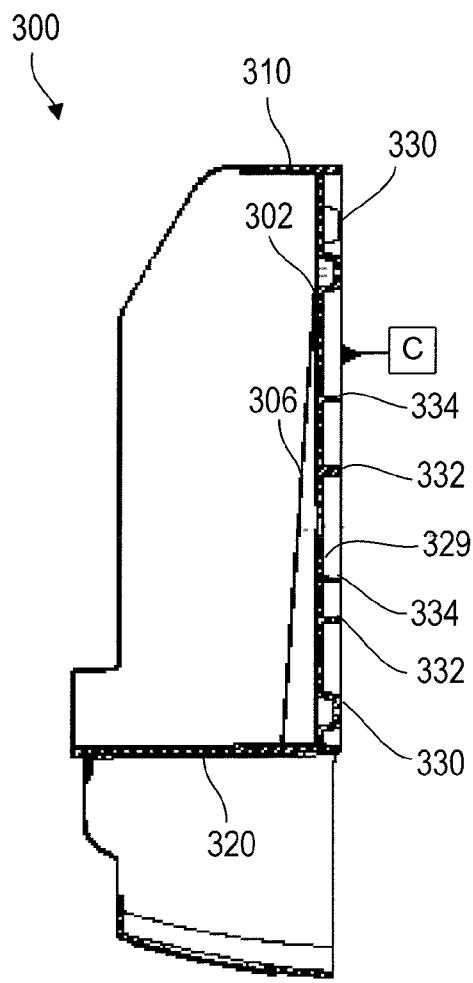
FIG. 13 is a cross-sectional side view of the wall plate of FIGS. 7-12.

FIGS. 10 and 11 are side views of wall plate 300, and FIG. 12 is a rear view of wall plate 300 showing mounting features/apertures 304 and ribs 306 (although not all instances of apertures 304 and ribs 306 are labeled), and FIG. 13 is a cross-sectional view of wall plate 300, taken through line B-B in FIG. 12. FIGS. 10-13 are best viewed together in light of the following description.

In one embodiment, wall plate 300 has a depth $d_{300}$ of about 5 to 6 inches, a first width $w_{300}$ of about 10 to 11 inches and a height $h_{300}$ of about 17 to 18 inches. In one aspect, $d_{300}$ is about 5.75 inches, $w_{300}$ is about 10.70 inches and $h_{300}$ is about 17.5 inches. Upper and lower cutouts/apertures 326 of each shelf 324 are spaced by a cutout-to-cutout distance $d_{C-C}$ of about 6-7 inches. In one aspect, $d_{C-C}$ is about 6.1 inches and a narrow neck 327 of each cutout 326 has a width of about 0.2-0.4 inches. An inner width $w_{312}$ of diaper compartment 312 is about 8.5 inches to 9 inches. A second wall plate 300 width $w_{314}$, corresponding to exterior width of wipe compartment 314, is about 8.1 inches. Centers of lower apertures 304 may be spaced about 0.8 inches to 1 inch from a lower edge 328 of back panel 302/floor panel 320.

As shown in FIG. 13, ribs 306 slope downwards and outwards from back panel 302 to advance stacked diapers towards a diaper retrieval slot in the cover of a diaper and wipe dispenser (e.g., slot 404 of cover 400, described below). Ceiling 310 of plate 300 extends about 1.5-2 inches from back panel 302, joining laterally with sidewalls 308, which extend further from back panel 302. Floor panel 320, back panel 302, sidewalls 308 and ceiling 310 may have a thickness of about 0.1-0.2 inches. In one aspect, wall plate 300 is about 0.125 inches thick overall. A rear surface 329 of back panel 302 includes a plurality of mounting extensions and/or peripheral edges that extend from surface 329 to facilitate mounting and/or lend structural strength to wall plate 300. Apertures 304, for example, open into rear protrusions 330. Where wall plate 300 is made from plastic, diagonally oriented ribs 332 may link protrusions 330 with an extrusion point (not shown), while horizontal ribs 334 join with vertically-oriented, raised peripheral edges of plate 300. Line "C" of FIG. 13 represents a plane containing the terminus of features 330-334.

Figure 14:
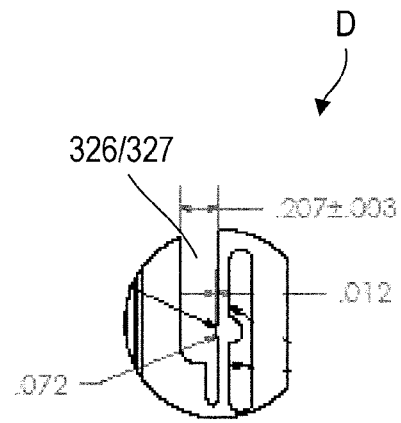
FIG. 14 shows exemplary detail of mounting features as illustrated in FIG. 12, for mounting the wall plate with a cover of a diaper and wipe dispensing system.

FIG. 14 shows additional detail and exemplary dimensions of area "D" in FIG. 12. Area D shows narrow neck 327 of a lower cutout 326, for mounting wall plate 300 with a cover 400, described below.

FIGS. 15-22 show a diaper and wipe dispenser cover 400, for mounting with wall plate 300 to form a diaper and wipe dispensing system (such as system 100/200). FIGS. 15-22 may be best viewed together with the following description.

Cover 400 may be molded from plastic, for example, BpA-, phthalate- and PVC-free plastic. In one embodiment, shown in FIG. 15, a front surface 402 of cover 400 includes a diaper retrieval slot 404 and a base cutout 406 for facilitating access to wipe retrieval slot 316 of wall plate 300 and/or for placement of cover 400 over and around wall plate 300. For example, an inner width of cutout 406 may be approximately equal to or just slightly larger than width $w_{312}$ of wall plate 300, such that a user may place cover 400 above wall plate 300 with wall plate 300 centered within cutout 406, and then slide cover 400 down into place over wall plate 300. A viewing slot 408 allows a user to see diapers within diaper compartment 312, to determine when compartment 312 is running low and should be refilled. Cover 400 has a height $h_{400}$ of about 18-19 inches, a width $w_{400}$ of about 14-15 inches and a depth $d_{400}$ of about 5-6 inches (see FIG. 17). In one aspect, $h_{400}$ is about 18.6 inches, $d_{400}$ is about 5.9 inches and $w_{400}$ is about 14.1 inches.

Figure 16:
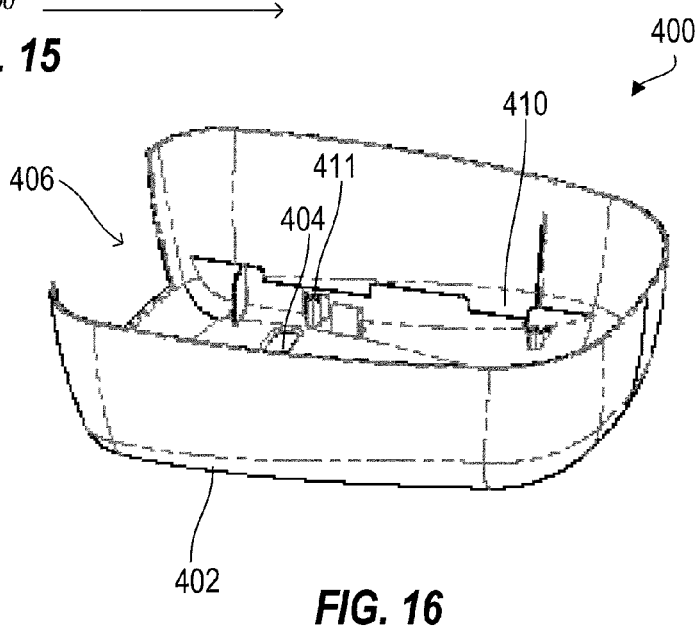
FIG. 16 is a side perspective view of the cover of FIG. 15, showing internal features for mounting with the wall plate of FIGS. 7-14.

FIG. 16 is a perspective view showing the interior of cover 400, including mounting features for mounting with wall plate 300. Mounting features may include one inner, lateral rail 410 configured with one upper and one lower pin 411 per side of cover 400. Lateral rails 410 are sized to accommodate/support shelves 324 of wall plate 300 (e.g., as cover 400 slides down over wall plate 300). Additional raised features such as lateral pins 411 that are sized to fit with cutouts or apertures 326 in shelves 324 may be provided along rails 410, such that cover 400 and wall plate 300 are further secured by a lock-and-key fit of such features.

Figure 15:
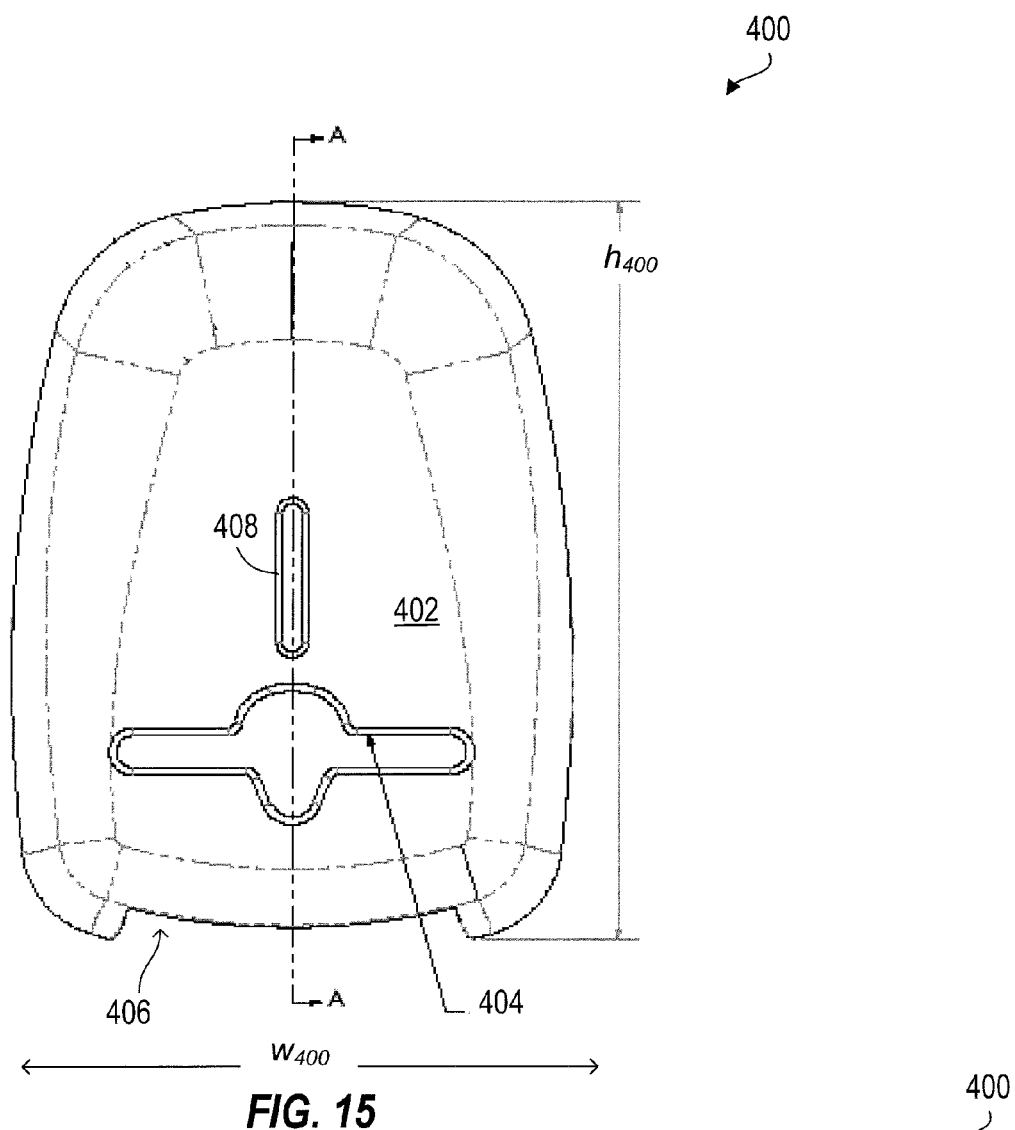
FIG. 15 is a front view of a cover for joining with the wall plate of FIGS. 7-14 to form a diaper and wipe dispensing system.
Figure 17:
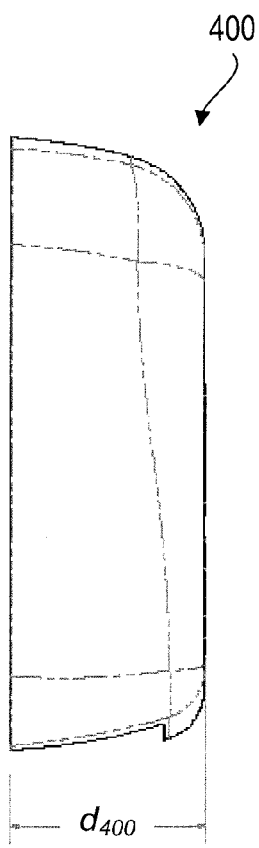
FIG. 17 is a side view of the cover of FIGS. 15 and 16.
Figure 18:
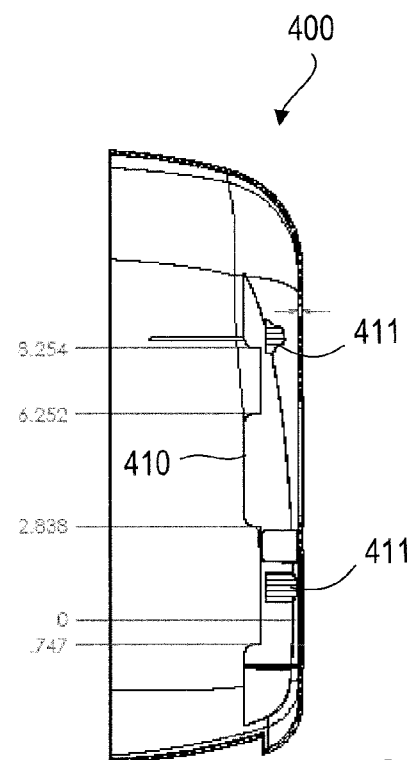
FIG. 18 is a cross sectional view of the cover of FIGS. 15-17, showing additional detail of internal mounting features.
Figure 26:
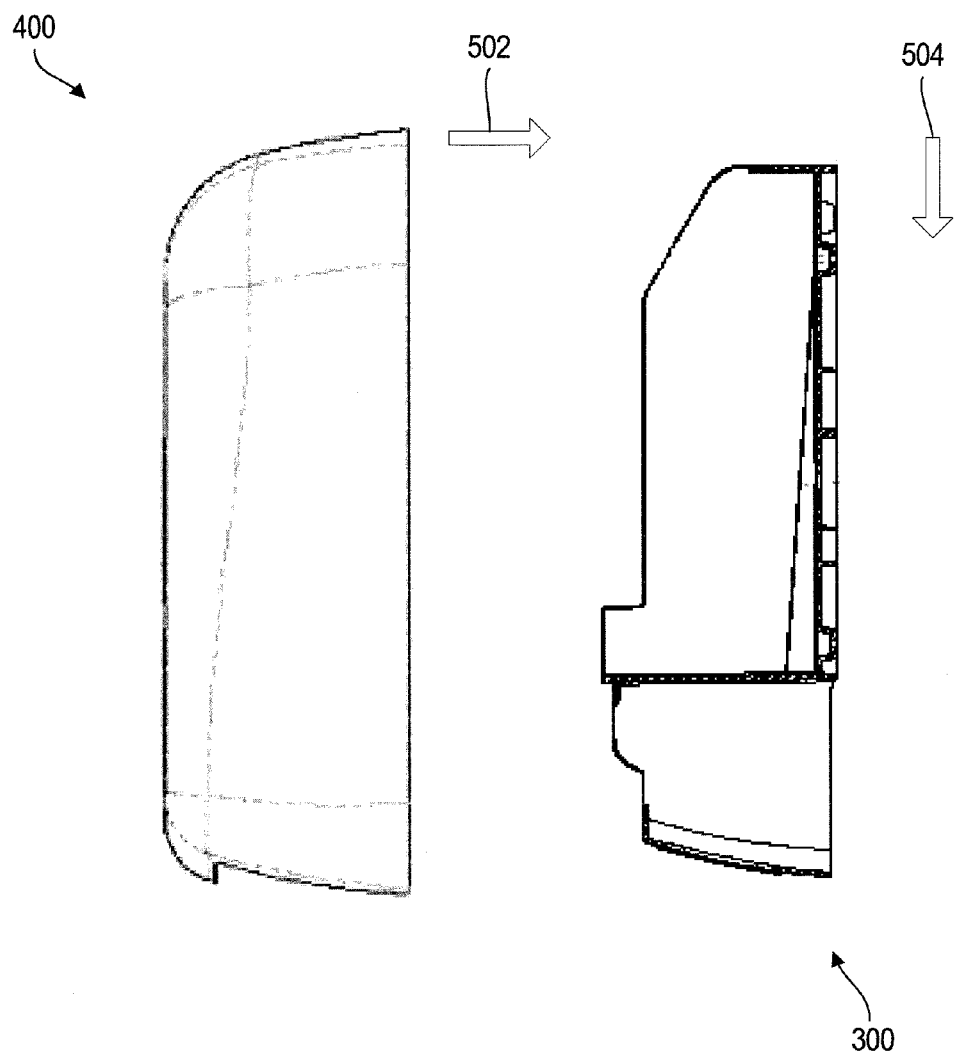
FIG. 26 is a side view of the wall plate of FIGS. 7-14 and the cover of FIGS. 15-17 illustrating mounting of the cover onto the wall plate.

FIG. 18 is a cross-sectional view taken along line A-A of FIG. 15, showing pins 411 configured with rail 410. FIG. 26 is a side view of the wall plate 300 of FIGS. 7-14 and the cover 400 of FIGS. 15-17 illustrating mounting of cover 400 onto wall plate 300. In one aspect, each rail 410 includes slots for housing base portions of pins 411, such that top portions of pins 411 extend from rail 410 to mate with cutouts 326. For example, cover 400 is aligned with, and positioned over, wall plate 300, as indicated by arrow 502, such that pins 411 mate with wide, upper portions of cutouts 326, and cover 400 is pulled or slid downwards to engage pins 411 in narrow necks 327 of each cutout, as indicated by arrow 504. Pins 411 may click into place within narrow necks 327. Gravity retains cover 400 in place with respect to wall plate 300, with each pin 411 "locked" into a respective neck 327.

Figure 19:
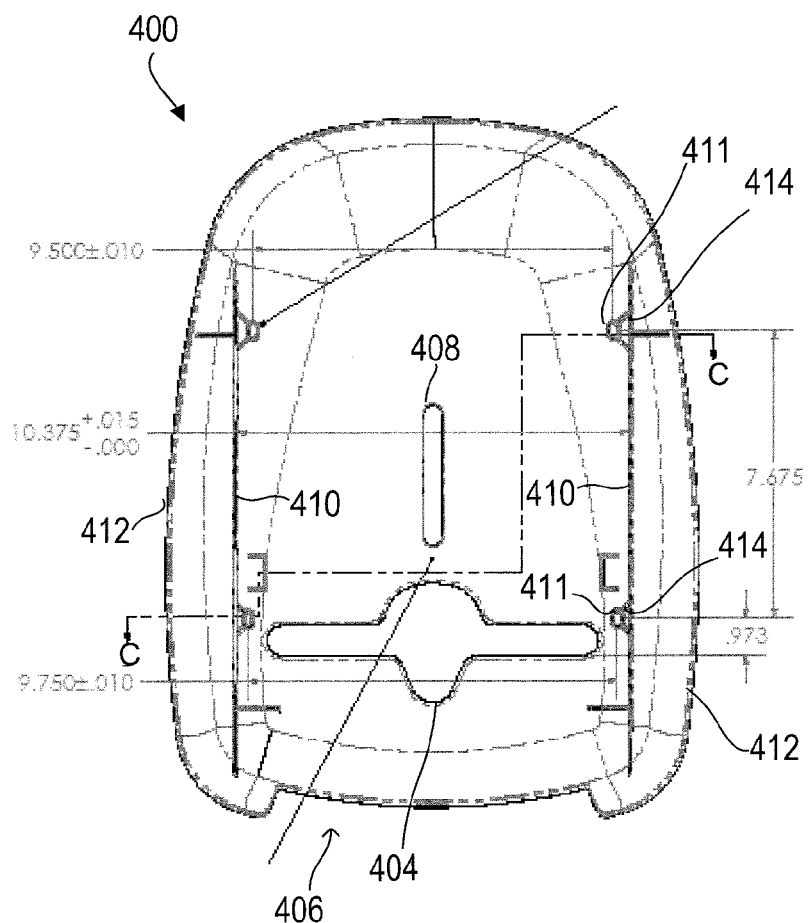
FIG. 19 is a back view of the front cover of FIGS. 15-18.
Figure 20:
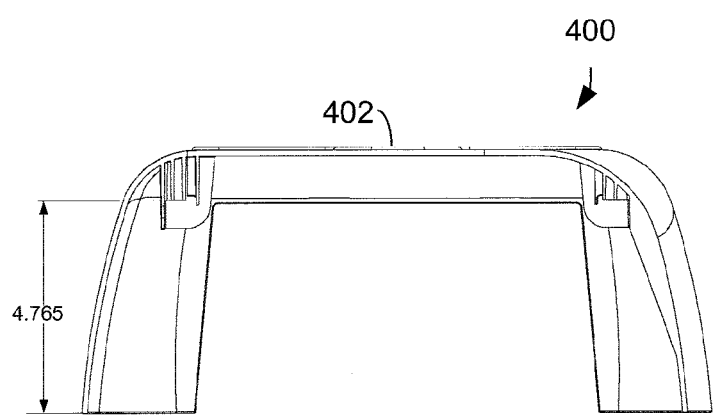
FIG. 20 is a cross-sectional view through the front cover of FIGS. 15-19.
Figure 21:
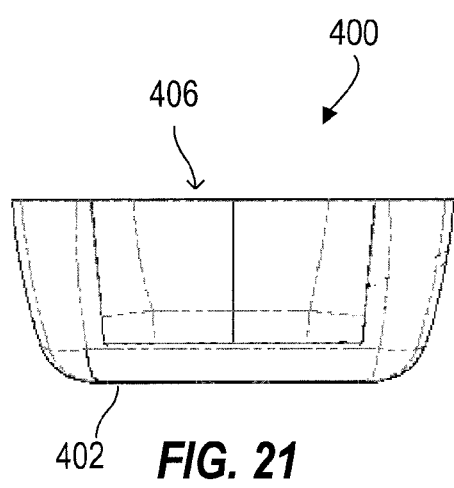
FIG. 21 is a bottom end view of the cover of FIGS. 15-20.
Figure 22:
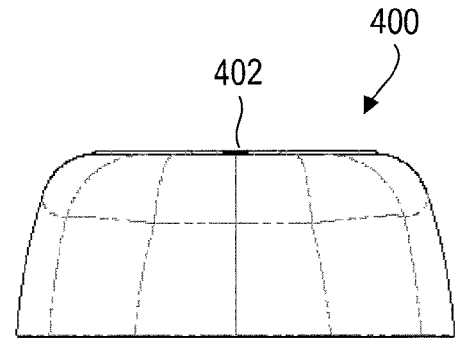
FIG. 22 is a top end view of the cover of FIGS. 15-21.

FIG. 19 shows cover 400 from the inside. Each lateral shelf 324 may attach with upper and lower pins 411 via a pair of bosses 414. FIG. 20 is a cross-sectional view taken along line C-C of FIG. 19. FIG. 21 is a bottom end view of cover 400, showing cutout 406, and FIG. 22 is a top end view of cover 400.

Figure 23:
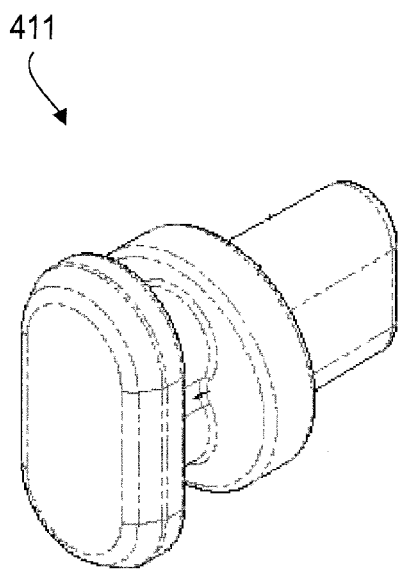
FIG. 23 is a front perspective view of a mounting pin of the cover of FIGS. 15-22, for fitting with the wall plate mounting features of FIG. 14.
Figure 24:
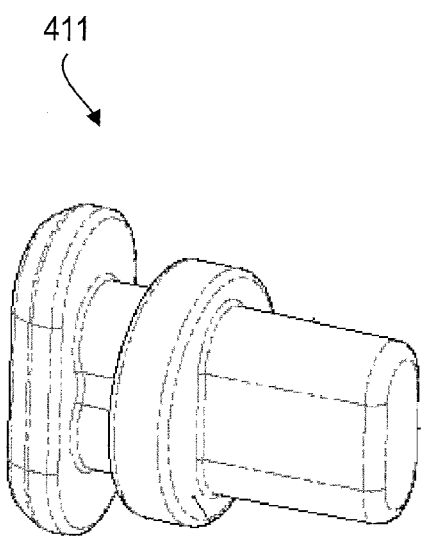
FIG. 24 is a rear perspective view of the mounting pin of FIG. 23.
Figure 25:
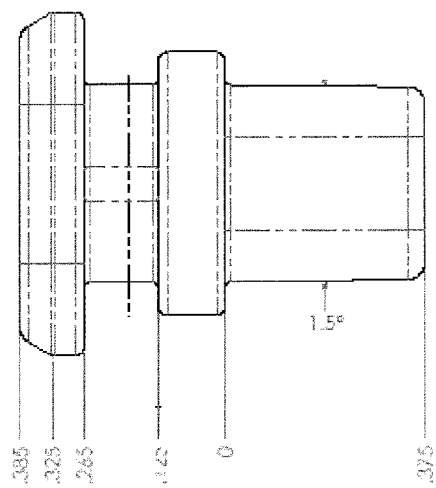
FIG. 25 is a schematic side view of the mounting pin of FIGS. 23 and 24.

FIGS. 23-25 show pin 411, with FIG. 25 showing exemplary pin dimensions.

It will be appreciated that FIGS. 1-25 show illustrative examples of diaper and wipe dispensing systems. Systems 100 and 200, wall plate 300 and cover 400 and their components are not limited to the particular shapes and dimensions shown in the figures or described herein above. It will be appreciated that many changes and modifications may be made to the disclosed diaper and wipe dispensing systems, without departing from the spirit and scope of this invention. For example, wipe slots 106, 206, 316 and/or cutout 406 may include a cover that is opened or removed to access stacked wipes within respective system 100/200 or a system formed by wall plate 300 and cover 400, to maintain moisture content of the baby wipes when the diaper and wipe dispensing system is not in use.

What is claimed is:

1. A diaper and wipe dispensing system comprising:
a housing formed by:
a rear wall plate for mounting with a vertical surface, and
a front cover configured to slidably mate with the rear wall plate;
an upper compartment within the housing, for holding stacked diapers;
a diaper slot in the housing, for accessing diapers within the upper compartment, the
diaper slot being formed through the front cover;
a lower compartment for holding baby wipes, the lower compartment being within the housing and being separated from the upper compartment by a floor panel, and
a wipe slot in the housing, for accessing wipes within the lower compartment, the wipe slot being formed through a bottom shelf of the rear wall plate;
wherein the cover slides down with respect to the wall plate to secure the cover with the wall plate and slides up with respect to the wall plate to facilitate removal of the cover and loading of diapers and wipes; and wherein a base of the front cover includes a cutout for facilitating access to the wipe slot through the front cover.

2. System of claim 1, the diaper slot being formed through the front cover, the slot facilitating retrieval of the diapers through the front cover.

3. System of claim 1, the upper compartment configured for holding horizontally stacked cloth or disposable diapers of any size.

4. System of claim 1, the diaper slot comprising a vertical cutout for facilitating removal of a diaper with a user's thumb and forefinger.

5. System of claim 1, the upper compartment comprising a floor having a cutout for facilitating removal of a diaper with the thumb and forefinger; the floor separating the upper compartment from the lower compartment.

6. System of claim 1, the lower compartment configured for accepting an inverted stack of self-feeding wipes.

7. System of claim 1, further comprising a secondary, partially or fully removable, reusable cover for fitting over the wipe slot to prevent leakage of wipe fluid from the housing.

8. System of claim 1, the wipe slot comprising an oval shape.

9. System of claim 1, the front cover and the wall plate comprising complementary lock-and-key features for releasably mating the cover with the wall plate.

10. System of claim 1, the rear wall plate including a back panel extending from a top of the diaper and wipe dispensing system to the floor panel, leaving the lower compartment open at a back surface of the system.

11. System of claim 1, the cover further comprising a vertical viewing slot above the diaper slot, for viewing diapers stacked within the housing.

12. System of claim 1, further comprising one or more raised vertical ribs extending from a back panel of the wall plate; the one or more ribs extending progressively farther from the back panel from a top to a bottom of the upper compartment, to shuttle stacked diapers towards the diaper slot in the front cover when the cover and the wall plate are joined.

13. A diaper and wipe dispensing system comprising:
a housing formed by:
a rear wall plate for mounting with a vertical surface and including left and right inner shelves, each shelf having an upper and a lower aperture, each aperture having a wider upper portion opening into a narrow, lower neck and;
a front cover configured to slidably mate with the rear wall plate and comprising left and right inner rails, each configured with one upper and one lower mounting pin; each mounting pin sized to mate with the wider upper portion of one of the wall plate apertures and slide downwards to lock into place within the narrow neck of the aperture, to secure the cover with the wall plate;
an upper compartment within the housing, for holding stacked diapers;
a diaper slot in the housing, for accessing diapers within the upper compartment;
a lower compartment for holding baby wipes, the lower compartment being within the housing and being separated from the upper compartment by a floor panel, and
a wipe slot in the housing, for accessing wipes within the lower compartment;
wherein the cover slides down with respect to the wall plate to secure the cover with the wall plate and slides up with respect to the wall plate to facilitate removal of the cover and loading of diapers and wipes.

14. System of claim 13, the cover further comprising a vertical viewing slot above the diaper slot, for viewing diapers stacked within the housing.

15. System of claim 13, further comprising one or more raised vertical ribs extending from a back panel of the wall plate; the one or more ribs extending progressively farther from the back panel from a top to a bottom of the upper compartment, to shuttle stacked diapers towards the diaper slot in the front cover when the cover and the wall plate are joined.

16. System of claim 13, the rear wall plate including a back panel extending from a top of the diaper and wipe dispensing system to the floor panel, leaving the lower compartment open at a back surface of the system.

17. System of claim 13, the diaper slot being formed through the front cover, the slot facilitating retrieval of the diapers through the front cover.

18. System of claim 13, the diaper slot comprising a vertical cutout for facilitating removal of a diaper with the thumb and forefinger.

19. System of claim 13, the upper compartment comprising a floor having a cutout for facilitating removal of a diaper with the thumb and forefinger; the floor separating the upper compartment from the lower compartment.

20. System of claim 13, the wipe slot comprising a partially or fully removable, reusable cover for preventing leakage of wipe fluid from the housing.

* * * * *